United States Patent [19]

Yamaka et al.

[11] Patent Number: 5,219,221
[45] Date of Patent: Jun. 15, 1993

[54] LAMP RETAINER OF LIGHT SOURCE DEVICE FOR ENDOSCOPE

[75] Inventors: Shoichi Yamaka; Junji Usami, both of Tokyo, Japan

[73] Assignee: Asahi Kogaku Kogyo Kabushiki Kaisha, Tokyo, Japan

[21] Appl. No.: 642,528

[22] Filed: Jan. 17, 1991

[30] Foreign Application Priority Data

Jan. 29, 1990 [JP] Japan ................... 2-18681

[51] Int. Cl.⁵ .................. H01R 33/02; F21V 29/00
[52] U.S. Cl. .................. 362/294; 362/373; 362/396; 439/486
[58] Field of Search .......... 362/32, 294, 373, 396, 362/263; 439/485, 486, 487

[56] References Cited

U.S. PATENT DOCUMENTS

| | | | |
|---|---|---|---|
| 1,758,775 | 5/1930 | Abbott | 439/485 |
| 2,662,220 | 12/1953 | Saari | 439/486 |
| 3,020,451 | 2/1962 | McAdam | 439/487 |
| 3,541,492 | 11/1970 | Fenn | 362/294 |
| 4,572,164 | 2/1986 | Yoshida et al. | 362/373 |
| 4,887,154 | 12/1989 | Wawro et al. | 362/294 |

FOREIGN PATENT DOCUMENTS

| | | | |
|---|---|---|---|
| 57-185303 | 11/1982 | Japan . | |
| 58-25582 | 6/1983 | Japan . | |
| 58-25583 | 6/1983 | Japan . | |
| 60-208005 | 10/1985 | Japan . | |
| 148613 | 12/1985 | Japan . | |
| 148614 | 12/1985 | Japan . | |
| 63-20023 | 6/1988 | Japan . | |
| 63-191311 | 12/1988 | Japan . | |
| 0280109 | 11/1990 | Japan | 362/294 |

*Primary Examiner*—Ira S. Lazarus
*Assistant Examiner*—Y. Quach
*Attorney, Agent, or Firm*—Sandler, Greenblum & Bernstein

[57] ABSTRACT

A lamp retainer of a light source device, which retains a light source lamp that has two electrodes, at least one of them being on the side thereof. The lamp retainer comprises an electrically conductive heat sink, and an electrically conductive electrode press device that is attached to the heat sink. The press device is biased to resiliently press the electrode from the side thereof, so that the electrode and the heat sink are electrically connected through the press device.

16 Claims, 8 Drawing Sheets

LAMP RETAINER OF LIGHT SOURCE DEVICE FOR ENDOSCOPE

BACKGROUND OF THE INVENTION

The present disclosure relates to subject matter contained in Japanese Patent application No. 2-18681 (filed on Jan. 29, 1990), which is expressly incorporated herein, by reference, in its entirety.

FIELD OF THE INVENTION

The present invention relates to a lamp retainer of a light source device that is used to supply illuminating light to an endoscope. More particularly, the present invention relates to a lamp retainer for retaining a light source lamp, which has a first electrode on the rear end portion and a second electrode on the side thereof.

DESCRIPTION OF THE PRIOR ART

FIGS. 7 and 8 show a lamp retainer of a light source device for an endoscope according to the prior art. Reference numeral 51 denotes a light source lamp. The light source lamp 51 has a light emitting window 52, a first electrode 53 with a stepped structure comprising a small-diameter portion 53a and a large-diameter portion 53b, and a second electrode 54 that is provided on the side of an end portion of the lamp 51, which is closer to the window 52.

A pair of first and second heat sinks 61 and 62 secure the light source lamp 51 in such a manner that the two heat sinks 61 and 62 are in contact with the first and second electrodes 53 and 54, respectively. The heat sinks 61 and 62 serve as both electrically conducting paths and heat dissipaters for the light source lamp 51.

A fixing screw 63 secures the light source lamp 51 to the first heat sink 61, such that the first electrode 53 and the first heat sink 61 are electrically connected to each other. A clamping screw 64 deforms the second heat sink 62 in a direction such that a slit 65, that is formed in the second heat sink 62, is narrowed. By tightening the screw 64, the second electrode 54 of the light source lamp 51 is clamped by the second heat sink 62, and thus, the light source lamp 51 is secured to the second heat sink 62.

However, if the clamping screw 64 is tightened too strong, the light source lamp 51 may be broken, and the clamping screw 64 must therefore be tightened with care, so as not to be overtightened. On the other hand, if the clamping screw 64 is not sufficiently tightened, a contact failure occurs between the second heat sink 62 and the second electrode 54. This results in the light source lamp 51 failing to be turned on.

Accordingly, the operation of attaching the light source lamp 51 to the heat sinks 61 and 62 is extremely delicate and difficult. The above-described problems, due to excessive or insufficient tightening of the clamping screw 64, have occurred frequently.

SUMMARY OF THE INVENTION

An object of the present invention is to provide a lamp retainer of a light source device, which enables a light source lamp to be readily attached to heat sinks with reliable electrical connections therebetween.

Other objects and advantages of the present invention will become apparent from the following detailed description of illustrated embodiments of the invention.

According to the present invention, there is provided a lamp retainer of a light source device, which retains a light source lamp that has two electrodes. At least one of the electrodes is on the side comprising an electrically conductive heat sink and an electrically conductive electrode press device that is attached to the heat sink. The press device is biased to resiliently press against the electrode from the side, so that the electrode and the heat sink are electrically connected through the press device.

BRIEF DESCRIPTION OF THE DRAWINGS

The present invention may be more fully understood from the description of preferred embodiments of the invention set forth below, together with the accompanying drawings, in which.

DETAILED DESCRIPTION OF THE EMBODIMENTS

Embodiments of the present invention will be described below with reference to the accompanying drawings.

Figure 1:
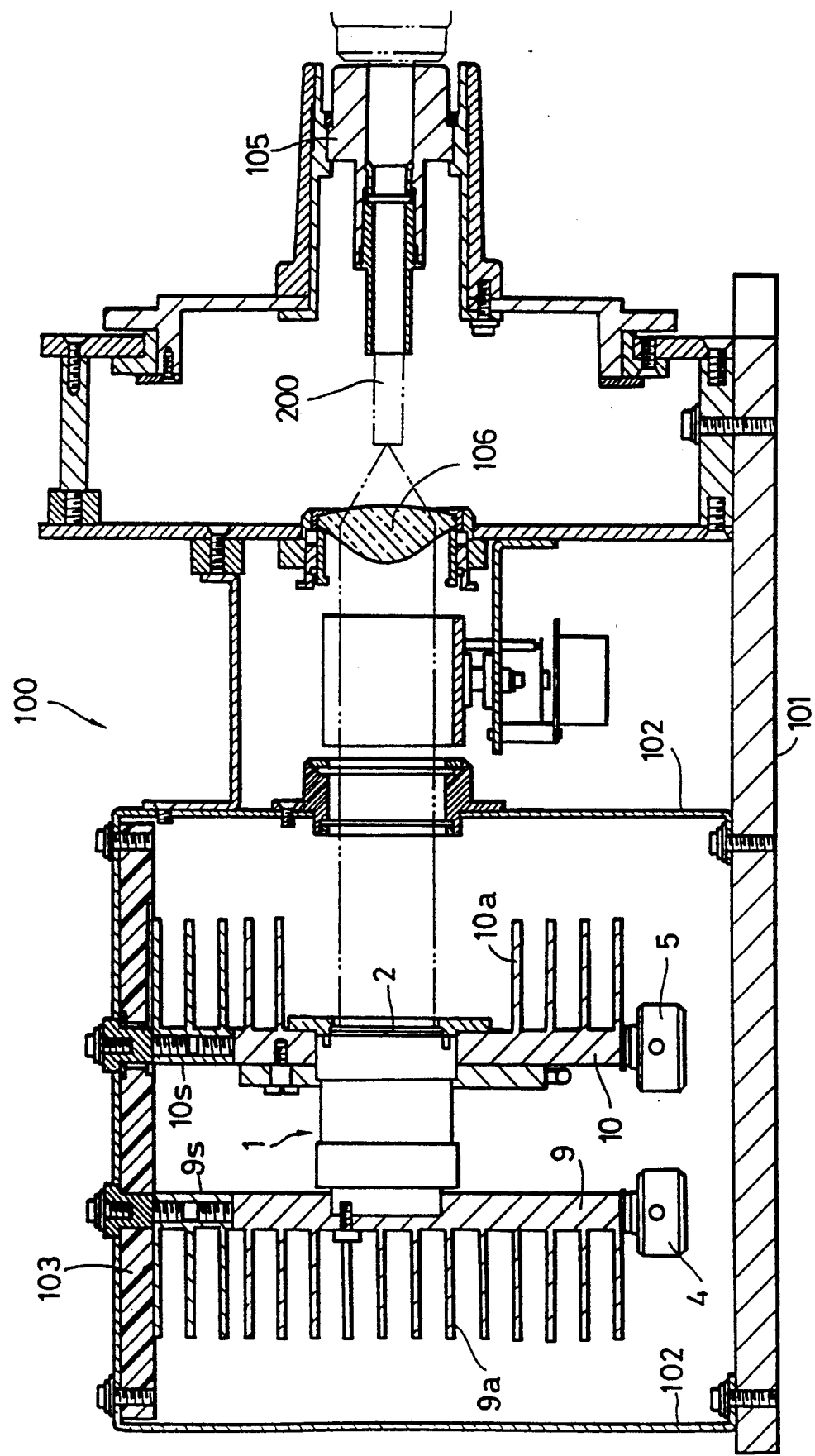
FIG. 1 is a sectional side view of a light source device for an endoscope according to a first embodiment of the present invention.

FIG. 1 shows a part of a light source device 100 for an endoscope. The light source device 100 has a floor plate 101, to which a frame 102 is secured. An electrical insulating base 103 is secured to the upper end of the frame 102, parallel to the floor plate 101.

A pair of first and second heat sinks 9 and 10 are suspended from the base 103. The heat sinks 9 and 10 are provided with a large number of cooling fins 9a and 10a, respectively. A xenon lamp 1 is retained by the two heat sinks 9 and 10. Both the heat sinks 9 and 10 are formed from a metallic material having good electrical and thermal conductivities.

A connector socket 105 is formed in front of a light emitting window 2 of the lamp 1, for externally inserting a light guide connector 200 of the endoscope. Illuminating light, that is emitted from the xenon lamp 1, is condensed onto the projecting end face of the light guide connector 200 by a condenser lens 106. The condensed light is transmitted through a light guide fiber bundle, and emitted to the outside, from the distal end of an insert part (not shown) of the endoscope. This illuminates the observation field of the endoscope.

Figure 2:
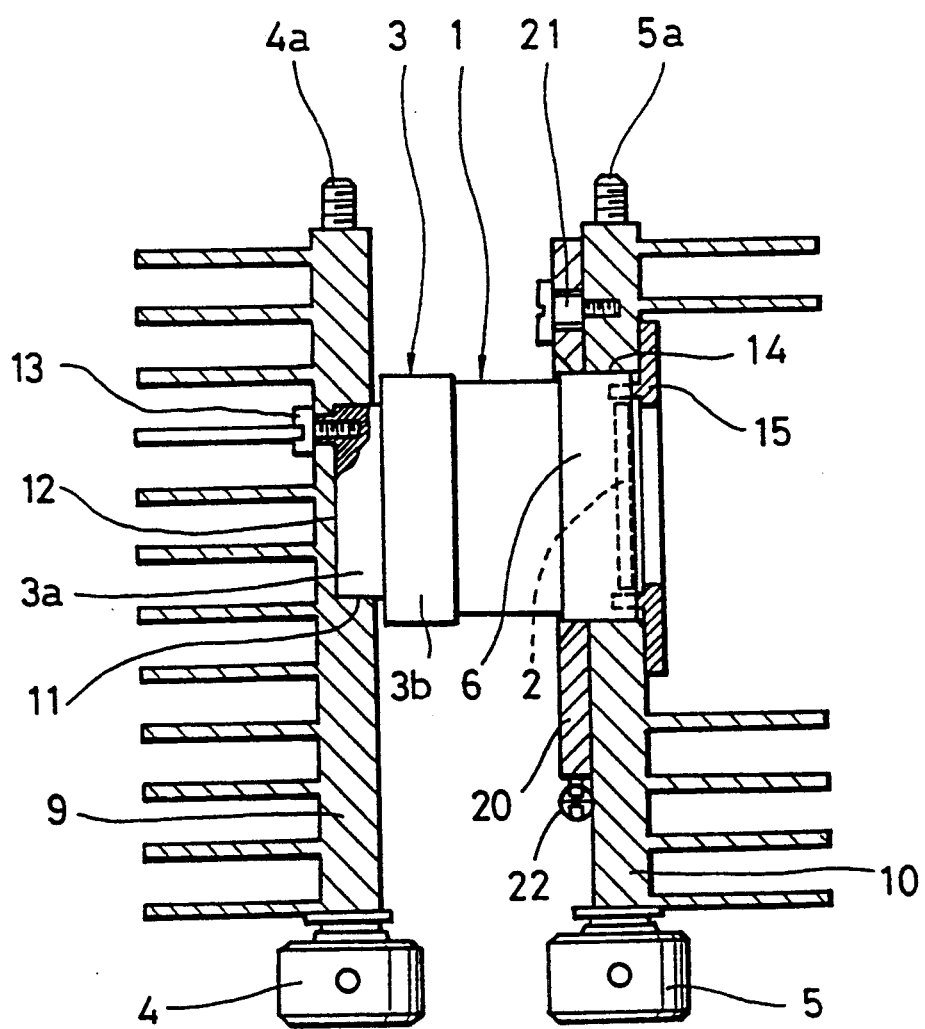
FIG. 2 is a sectional side view of a lamp retainer according to the first embodiment of the present invention.

FIG. 2 shows the heat sinks 9 and 10.

The window 2, for emitting illuminating light forwardly, is formed in the front end face of the cylindrical xenon lamp 1. A first electrode 3 is attached to the rear end portion of the lamp 1. The first electrode 3 has a stepped structure comprising a small-diameter portion 3a which is closer to the outer end of the electrode 3 and a large-diameter portion 3b which is contiguous with the inner end of the small-diameter portion 3a.

An annular second electrode 6 is provided on the outer periphery of the front end portion of the xenon lamp 1. The electrode 6 has substantially the same outer diameter as that of the large-diameter portion 3b.

The first and second heat sinks 9 and 10, which are spaced apart from each other, are suspended from the underside of the base 103 through respective sub-heat sinks 9s and 10s, which are shown in FIG. 1. Reference numerals 4 and 5 denote mounting bolts, whose distal end portions 4a and 5a are screwed into the sub-heat sinks 9s and 10s, respectively.

The first heat sink 9, which is closer to the rear end of the light source device, is provided with a socket 11 for insertion of the small-diameter portion 3a of the first electrode 3. The inner end of the socket 11 is provided with a stopper 12, that abuts against the rear end face of the small-diameter portion 3a.

Accordingly, the small-diameter portion 3a of the first electrode 3 is tightly fitted into the socket 11, with the rear end face of the small-diameter portion 3a pressed against the stopper 12. This enables the first electrode 3 to be set in position.

Then, a screw 13 is screwed into the rear end portion of the first electrode 3 of the xenon lamp 1 through a bore that is formed in the first heat sink 9. Thus enabling the xenon lamp 1 to be positioned and secured to the first heat sink 9. In addition, the first heat sink 9 and the first electrode 3 are electrically connected to each other.

In the meantime, the second heat sink 10, which is forward of the first heat sink 9, is formed with a guide bore 14, which can loosely receive the second electrode 6 of the xenon lamp 1, so that it is removable. A positioning member 15 is attached to the front face of the second heat sink 10 by means of screws (not shown). This enables the positioning member 15 to fit loosely to the front end portion of the xenon lamp 1, allowing it to be positioned.

Figure 3:
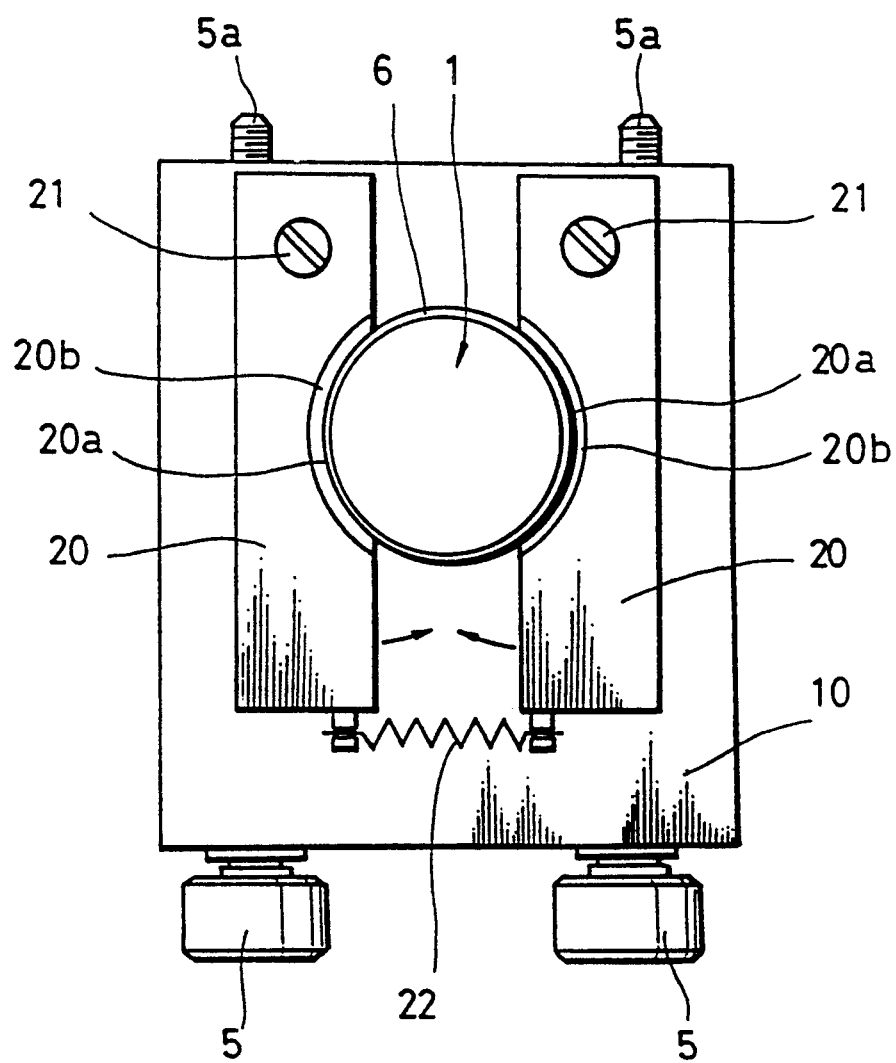
FIG. 3 is a rear view of a second heat sink in the first embodiment of the present invention.

As shown in FIG. 3, a pair of right and left press members 20, which are formed from electrically conductive metal plates, are attached to the back side of the second heat sink 10, in such a manner as to be pivotable about respective pivot shafts 21. Each press member 20 is cut circularly so as to come into close contact with the second electrode 6 of the xenon lamp 1. Reference numeral 20a denotes the circular cut portions.

In addition, a tension coil spring 22 is stretched between the two press members 20 to bias them toward each other, so as to clamp the xenon lamp 1 from both sides. Accordingly, the xenon lamp 1 is secured to the second heat sink 10 with the second electrode 6 being resiliently pressed from both sides by the press members 20.

Figure 4:
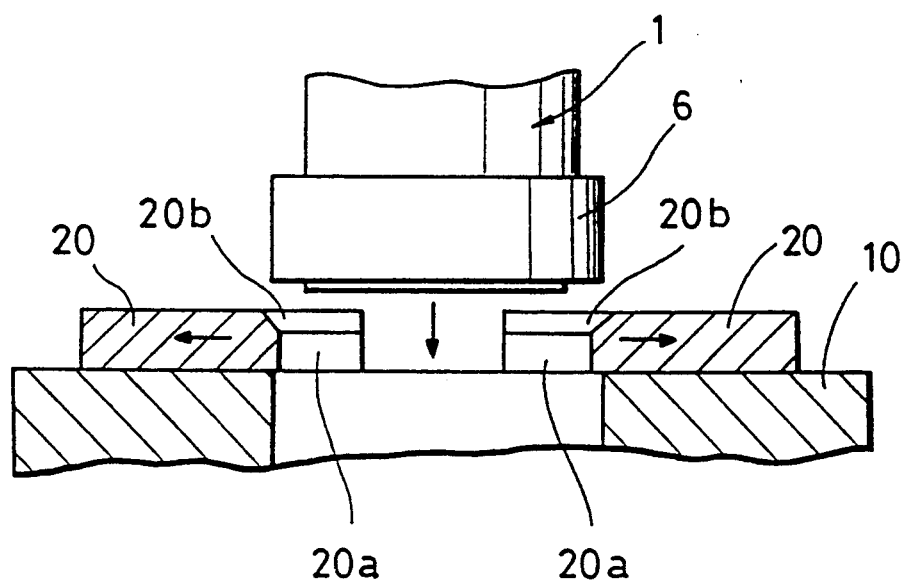
FIG. 4 is a fragmentary plan view of the lamp retainer according to the first embodiment of the present invention.

It should be noted that a chamfer 20b is formed along the edge of the cut portion 20a of each press member 20. Accordingly, when the second electrode 6 of the xenon lamp 1 is axially inserted into the area defined between the cut portions 20a, as shown in FIG. 4, the lamp 1 is guided by the chamfers 20b, while the two press members 20 open, so that the second electrode 6 can be inserted with ease.

In this way, the xenon lamp 1 is secured to the second heat sink 10 by the press members 20. In this state, an electrical connection is reliably made between the second electrode 6 and the second heat sink 10 through the press members 20. In addition, heat that is generated from the second electrode 6 is conducted to the second heat sink 10 through the press members 20 for dissipation.

Figure 5:
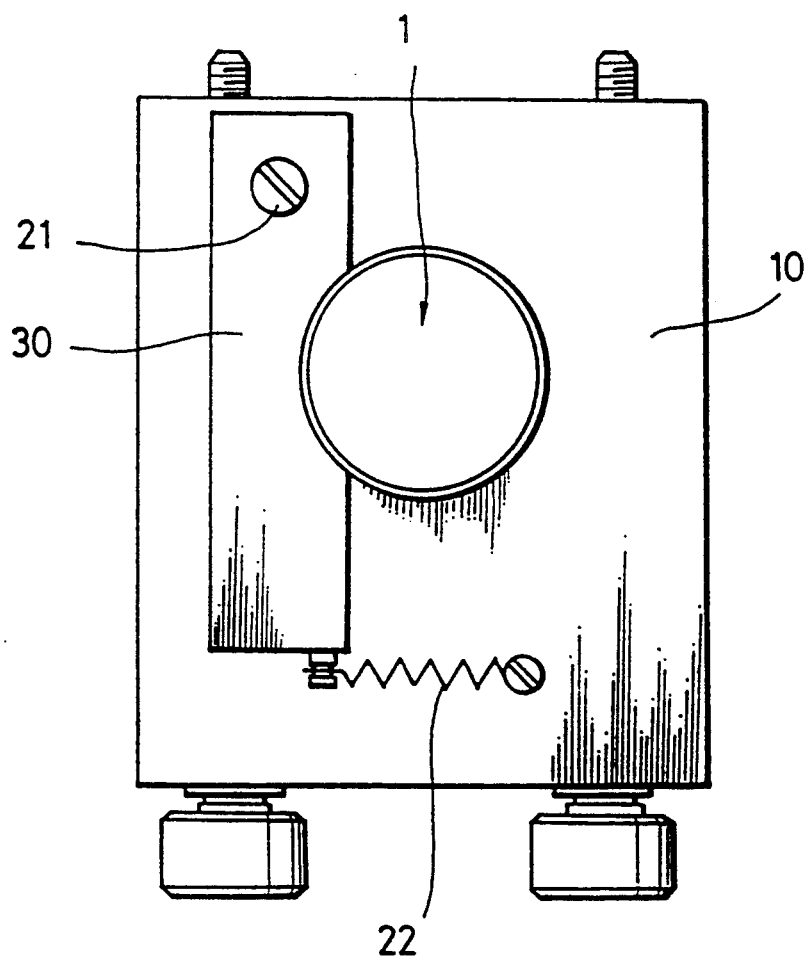
FIG. 5 is a rear view of a second heat sink in a second embodiment of the present invention.
Figure 6:
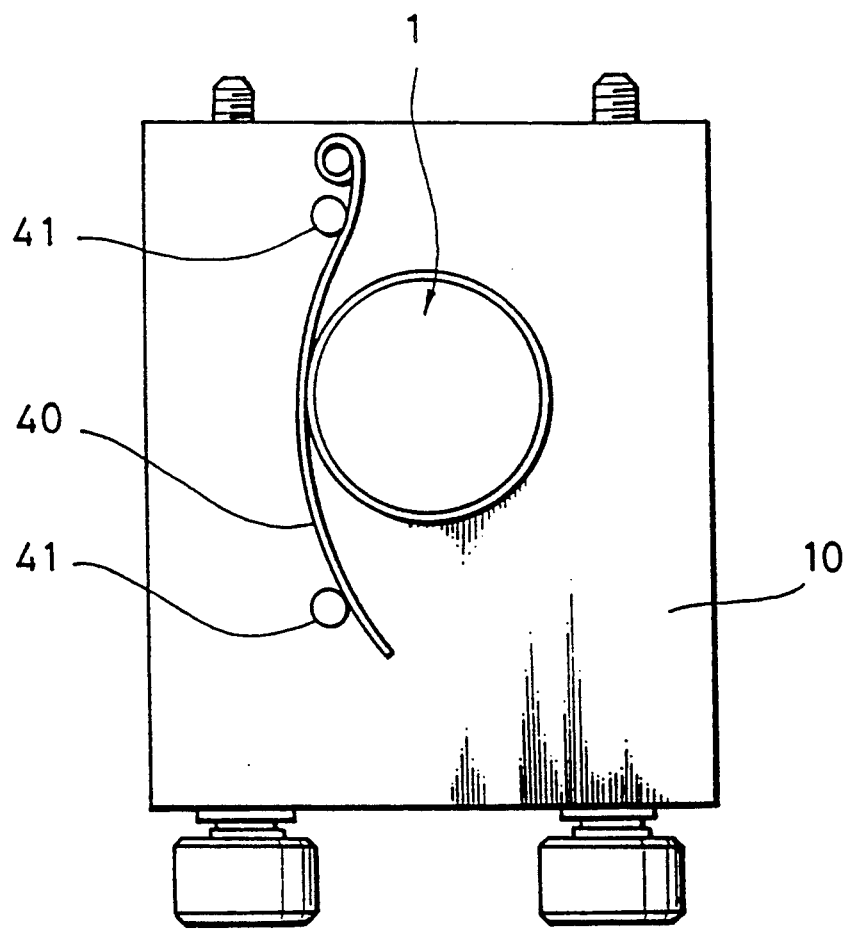
FIG. 6 is a rear view of a second heat sink in a third embodiment of the present invention.
Figure 7:
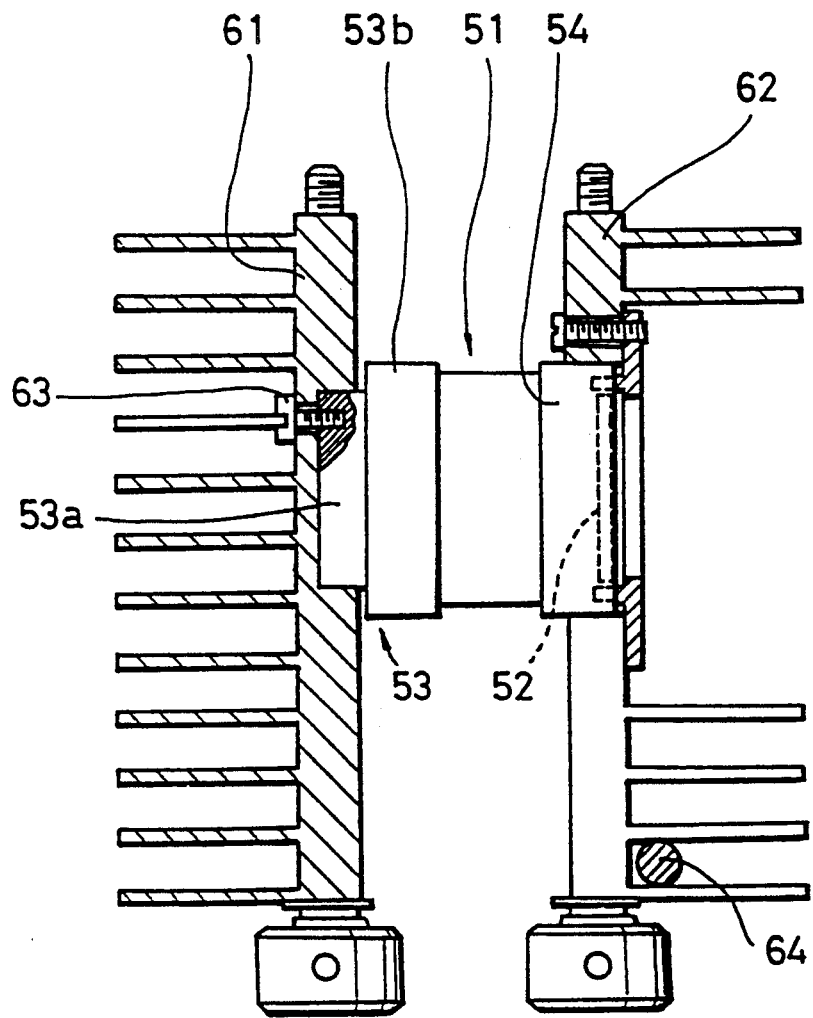
FIG. 7 is a sectional side view of a lamp retainer according to the prior art.
Figure 8:
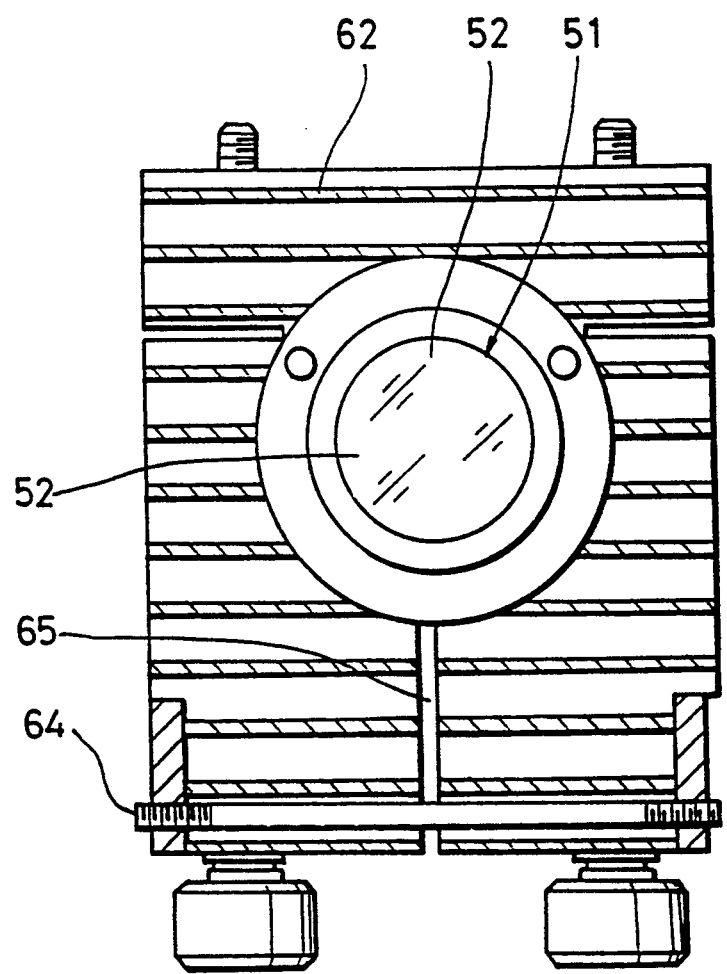
FIG. 8 is a sectional front view of the prior art shown in FIG. 7.

FIG. 5 shows a second embodiment of the present invention, which employs only one press member 30. FIG. 6 shows a third embodiment of the present invention, in which a press member 40 itself is formed from a resilient metal.

In FIG. 5, one end of the tension coil spring 22 is secured to the second heat sink 10. In FIG. 6, stoppers 41 are provided on the back side of the second heat sink 10 to elastically deform the press member 40.

According to the present invention, at least one press member, that is attached to the second heat sink resiliently presses the second electrode that is formed on the side of the light source lamp, thereby securing the light source lamp to the second heat sink. Accordingly, the light source lamp can be secured, with the second heat sink and the second electrode electrically connected together reliably, without any destructive force to the lamp. Thus, it is possible to eliminate the problems of breakage and contact failure of the light source lamp.

While the invention has been described by reference to specific embodiments chosen for purposes of illustration, it should be apparent that numerous modifications could be made thereto by those skilled in the art without departing from the basic concept and scope of the invention.

We claim:

1. A lamp retainer of a light source device for retaining a light source lamp having at least one side, the light source lamp further having two electrodes, at least one of said electrodes having a side portion, said lamp retainer comprising:

an electrically conductive heat sink; and an electrically conductive electrode press means, said electrically conductive electrode press means comprising a portion which is electrically connected to said electrically conductive heat sink; a portion which is electrically connected to said at least one of said electrodes and is movable with respect to said electrically conductive heat sink; and a spring portion which biases said portion which is electrically connected to said at least one of said electrodes, in order to press said at least one of said electrodes, said electrically conductive electrode press means being biased to resiliently press said at least one of said electrodes from said side portion of said at least one of said electrodes, so that said at least one of said electrodes and said electrically conductive heat sink are electrically connected through said electrically conductive electrode press means.

2. A lamp retainer of a light source device for retaining a light source lamp according to claim 1, wherein said light source lamp has at least one side, and said at least one of said electrodes which is pressed by said electrically conductive electrode press means is on said at least one side of said light source lamp.

3. A lamp retainer of a light source device for retaining a light source lamp according to claim 1, wherein said at least one electrode is integrally provided on an outer periphery of at least one said side of said light source lamp.

4. A lamp retainer of a light source device for retaining a light source lamp according to claim 1, wherein said portion which is electrically connected to said at least one of said electrodes is movable against said electrically conductive heat sink.

5. A lamp retainer of a light source device for retaining a light source lamp that has a rear end portion and at least one side, a first electrode on said rear end portion and a second electrode having at least one side on said at least one side of said light source lamp, said lamp retainer comprising:
- a first electrically conductive heat sink that secures said rear end portion of said light source lamp, and that is electrically connected to said first electrode;
- a second electrically conductive heat sink that is spaced apart from said first electrically conductive heat sink; and
- electrically conductive electrode press means that is attached to said second electrically conductive heat sink, said electrically conductive electrode press means comprising a portion which is electrically connected to said second electrically conductive heat sink; a portion which is electrically connected to said at least one side of said second electrode and is movable with respect to said second electrically conductive heat sink; and a spring portion which biases said portion which is electrically connected to said second electrode, in order to press said second electrode, from said at least one side of said second electrode, so that said second electrode and said second electrically conductive heat sink are electrically connected through said electrically conductive electrode press means.

6. A lamp retainer of a light source device for retaining a light source lamp according to claim 5, wherein said second electrode is integrally provided on an outer periphery of at least one said side of said light source lamp.

7. A lamp retainer of a light source device for retaining a light source lamp according to claim 5, wherein said portion which is electrically connected to at least one said side of said second electrode is movable against said second electrically conductive heat sink.

8. A lamp retainer of a light source device for an endoscope, which retains a light source lamp having a rear end portion and at least one side, a first electrode on said rear end portion and a second electrode having at least one side on said side at least one of said light source lamp, comprising:
- a first electrically conductive heat sink that secures said rear end portion of said light source lamp, and that is electrically connected to said first electrode;
- a second electrically conductive heat sink that is spaced apart from said first electrically conductive heat sink; and
- electrically conductive electrode press means that is attached to said second electrically conductive heat sink, said electrically conductive electrode press means comprising a portion which is electrically connected to said second electrically conductive heat sink; a portion which is electrically connected to said at least one side of said second electrode and is movable with respect to said second electrically conductive heat sink, and a spring portion which biases said portion which is electrically connected to said second electrode, in order to press said second electrode, from said at least one side of said second electrode, so that said second electrode and said second electrically conductive heat sink are electrically connected through said electrically conductive press means.

9. A lamp retainer of a light source device for an endoscope according to claim 8, wherein said rear end portion of said light source lamp is secured to said first electrically conductive heat sink by a screw.

10. A lamp retainer of a light source device for an endoscope according to claim 3, wherein said second electrode is inserted into a bore that is formed in said second electrically conducive heat sink.

11. A lamp retainer of a light source device for retaining a light source lamp according to claim 10, wherein said bore is chamfered.

12. A lamp retainer of a light source device for an endoscope according to claim 3, wherein said electrically conductive electrode press means are provided at both sides of said light source lamp and biased to clamp it from both sides.

13. A lamp retainer of a light source device for an endoscope according to claim 3, wherein said electrically conductive electrode press means is formed from a resilient metal.

14. A lamp retainer of a light source device for retaining a light source lamp according to claim 8, wherein said second electrode is integrally provided on an outer periphery of least one said side of said light source lamp.

15. A lamp retainer of a light source device for retaining a light source lamp according to claim 8, wherein said electrically conductive electrode press means are provided at only one side of said second electrode and biased to clamp said second electrode from one side.

16. A lamp retainer of a light source device for retaining a light source lamp according to claim 8, wherein said portion which is electrically connected to at least one said side of said second electrode is movable against said second electrically conductive heat sink.

* * * * *

UNITED STATES PATENT AND TRADEMARK OFFICE
CERTIFICATE OF CORRECTION

PATENT NO. : 5,219,221

DATED : June 15, 1993

INVENTOR(S) : S. Yamaka et al

Page 1 of 2

It is certified that error appears in the above-indentified patent and that said Letters Patent is hereby corrected as shown below:

At column 4, line 64 (claim 3, line 4) of the printed patent, delete "said" before "side" and insert ---said--- before "at least one".

At column 5, line 37 (claim 6, line 4) of the printed patent, delete "said" before "side" and insert ---said--- before "at least one".

At column 5, lines 41-42 (claim 7, lines 3-4) of the printed patent, delete "said" before "side" and insert ---said--- before "at least one".

At column 6, line 19 (claim 8, line 28) of the printed patent, insert ---electrode--- before "press".

At column 6, line 25 (claim 10, line 2) of the printed patent, change "claim 3" to ---claim 8---.

At column 6, line 32 (claim 12, line 2) of the printed patent, change "claim 3" to ---claim 8---.

UNITED STATES PATENT AND TRADEMARK OFFICE
CERTIFICATE OF CORRECTION

PATENT NO. : 5,219,221

DATED : June 15, 1993

INVENTOR(S) : S. Yamaka et al

It is certified that error appears in the above-indentified patent and that said Letters Patent is hereby corrected as shown below:

At column 6, line 37 (claim 13, line 2) of the printed patent, change "claim 3" to ---claim 8---.
At column 6, line 43 (claim 14, line 4) of the printed patent, delete "said" before "side" and insert ---said--- after "periphery of".
At column 6, line 43 (claim 14, line 4) of the printed patent, insert ---at--- before "least".
At column 6, lines 51-52 (claim 16, lines 3-4) of the printed patent, delete "said" after "one" (line 52) and insert ---said--- before "at least" (line 51).

Signed and Sealed this

Twenty-seventh Day of September, 1994

Attest:

BRUCE LEHMAN

Attesting Officer

Commissioner of Patents and Trademarks